United States Patent
Al Hasan et al.

(10) Patent No.: US 11,621,075 B2
(45) Date of Patent: Apr. 4, 2023

(54) SYSTEMS, METHODS, AND APPARATUS FOR DIAGNOSTIC INFERENCING WITH A MULTIMODAL DEEP MEMORY NETWORK

(71) Applicant: KONINKLIJKE PHILIPS N.V., Eindhoven (NL)

(72) Inventors: Sheikh Sadid Al Hasan, Cambridge, MA (US); Siyuan Zhao, Worcester, MA (US); Oladimeji Feyisetan Farri, Yorktown Heights, NY (US); Kathy Mi Young Lee, Westford, MA (US); Vivek Datla, Ashland, MA (US); Ashequl Qadir, Melrose, MA (US); Junyi Liu, Windham, NH (US); Aaditya Prakash, Waltham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1063 days.

(21) Appl. No.: 16/330,174

(22) PCT Filed: Sep. 5, 2017

(86) PCT No.: PCT/EP2017/072136
§ 371 (c)(1),
(2) Date: Mar. 4, 2019

(87) PCT Pub. No.: WO2018/046452
PCT Pub. Date: Mar. 15, 2018

(65) Prior Publication Data
US 2019/0221312 A1    Jul. 18, 2019

Related U.S. Application Data

(60) Provisional application No. 62/384,235, filed on Sep. 7, 2016.

(51) Int. Cl.
| | |
|---|---|
| G16H 50/20 | (2018.01) |
| G16H 15/00 | (2018.01) |
| G06N 3/04 | (2006.01) |
| G06N 3/049 | (2023.01) |

(52) U.S. Cl.
CPC ............ *G16H 50/20* (2018.01); *G06N 3/049* (2013.01); *G06N 3/0454* (2013.01); *G06N 3/0481* (2013.01); *G16H 15/00* (2018.01)

(58) Field of Classification Search
None
See application file for complete search history.

(56) References Cited

U.S. PATENT DOCUMENTS

2015/0112224 A1*  4/2015  Super .................. A61B 3/02
                                                600/558
2017/0372475 A1* 12/2017  Gulsun ................ G06T 7/0012

FOREIGN PATENT DOCUMENTS

| CN | 105760507 A | 7/2016 |
|----|-------------|--------|
| CN | 106599198 A | 4/2017 |

(Continued)

OTHER PUBLICATIONS

Learning to Read Chest X-Rays: Recurrent Neural Cascade Model for Automated Image Annotation Shin et al. (Year: 2016).*

(Continued)

*Primary Examiner* — Delomia L Gilliard (57) ABSTRACT

The described embodiments relate to systems, methods, and apparatus for providing a multimodal deep memory network (200) capable of generating patient diagnoses (222). The multimodal deep memory network can employ different neural networks, such as a recurrent neural network and a convolution neural network, for creating embeddings (204, 214, 216) from medical images (212) and electronic health records (206). Connections between the input embeddings (204) and diagnoses embeddings (222) can be based on an (Continued)

amount of attention that was given to the images and electronic health records when creating a particular diagnosis. For instance, the amount of attention can be characterized by data (110) that is generated based on sensors that monitor eye movements of clinicians observing the medical images and electronic health records. Resulting patient diagnoses can be provided according to a predetermined classification of weights, or a compilation of words that are generated over multiple iterations of the multimodal deep memory network.

20 Claims, 5 Drawing Sheets

(56) References Cited

FOREIGN PATENT DOCUMENTS

| CN | 106650756 A | 5/2017 |
|---|---|---|
| CN | 106777125 A | 5/2017 |

OTHER PUBLICATIONS

Latent feature representation with stacked auto-encoder for AD/MCI diagnosis. Suk et al. (Year: 2013).*

Shin, et al., "Learning to Read Chest X-Rays: Recurrent Neural Cascade Model for Automated Image Annotation", 2016 IEEE Conference on Computer Vision and Pattern Recognition, Jun. 27, 2016, pp. 2497-2506.

Suk, et al., "Latent feature representation with stacked auto-encoder for AD/MCI diagnosis", Brain Structure and Function, vol. 220, No. 2, Dec. 22, 2013, pp. 841-859.

Calixto, et al., "Doubly-Attentive Decoder for Multi-modal Neural Machine Translation", 11 pages. (Abstract).

Lu, et al., "Hierarchical Question-Image Co-Attention for Visual Question Answering", 11 pages. (Abstract).

Xu, et al., "Show, Attend and Tell: Neural Image Caption Generation with Visual Attention", Neural Image Caption Generation with Visual Attention, 10 pages. (Abstract).

Yang, et al., "Stacked Attention Networks for Image Question Answering", 9 pages (Abstract).

* cited by examiner

SYSTEMS, METHODS, AND APPARATUS FOR DIAGNOSTIC INFERENCING WITH A MULTIMODAL DEEP MEMORY NETWORK

CROSS-REFERENCE TO PRIOR APPLICATIONS

This application is the U.S. National Phase application under 35 U.S.C. § 371 of International Application No. PCT/EP2017/072136, filed on Sep. 5, 2017, which claims the benefit of Provisional Application Ser. No. 62/384,235, filed Sep. 7, 2016. These applications are hereby incorporated by reference herein, for all purposes.

TECHNICAL FIELD

The embodiments described herein generally relate to artificial intelligence for assisting with diagnosing medical patients. More specifically, but not exclusively, systems, methods, and apparatus are set forth for providing a multimodal deep memory network that is trained to consider an amount of attention given to a medical document or image when providing a patient diagnosis.

BACKGROUND

Clinicians are often overburdened by the amount of data available to understand a condition of a patient, as much of the data comes from historical medical records of the patient and extensive databases of medical knowledge. As a result, a clinician may take much longer providing a diagnosis, thereby increasing costs of treatment and wait times for patients. Furthermore, although clinical guidelines can assist clinicians in identifying a correct diagnosis for a patient, such guidelines may not consider certain mediums of medical data beyond textual data. As a result, a clinician can omit certain conditions from the diagnoses, which can lead to less desirable patient outcomes.

SUMMARY

The implementations set forth herein relate to diagnostic inferencing with a multimodal deep memory network. In some implementations, a method performed by one or more processors is set forth as including steps or blocks such as generating a first set of embeddings from an image received at a first neural network, and generating a second set of embeddings from a document received at a second neural network. Each of the image and the document can be associated with a medical patient. The steps can further include applying the first set of embeddings and the second set of embeddings as input across a trained model that includes multiple different diagnosis embeddings. The trained model can include key embeddings and value embeddings that are associated with weights that are based at least in part on an amount of attention given to a portion of medical data from which the key embeddings and the value embeddings are generated. The steps can also include generating weights for the multiple different diagnosis embeddings based on a correlation between the first set of embeddings and the second set of embeddings, and the key embeddings and the value embeddings. Furthermore, the steps can include providing a patient diagnosis for the medical patient at least based on the generated weights for the multiple different diagnosis embeddings. The amount of attention can correspond to attention data that is based on an amount of eye movement exhibited by a user accessing the medical data. Generating the second set of embeddings can include generating an input value embedding from a section heading of the document, and generating input key embeddings from content that is separate from the section heading of the document. The medical data, from which the key embeddings and the value embeddings are generated, can include a medical image with a corresponding textual description. The second neural network can be a bi-directional recurrent neural network, and the document can correspond to an electronic health record. The first neural network can be a convolution neural network.

The method steps can be performed in any ordered, and are not limited by the order set forth herein. Furthermore, the methods steps can be embodied as instructions and stored in a memory of a computing device. The computing device can include one or more processors that, when executing the instructions, cause the computing device to perform the method steps. The methods steps can be embodied in instructions that are stored in a non-transitory computer readable medium.

Additionally the term "controller" is used herein generally to describe various apparatus relating to the operation of one or more electrical components or software components. A controller can be implemented in numerous ways (e.g., such as with dedicated hardware) to perform various functions discussed herein. A "processor" is one example of a controller, which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF THE INVENTION

The implementations set forth herein relate to systems, methods, and apparatuses for providing diagnosis support for clinicians using a multimodal deep learning model. Specifically, the multimodal deep learning model can use both textual data inputs and image data inputs for providing one or more diagnoses for use by a clinician. The textual data can be provided to one or more neural networks of the multimodal deep learning model in order to create embeddings from the textual data (e.g., documents corresponding to electronic health records). The neural networks for creating the embeddings can include a bi-directional recurrent neural network and/or a convolution neural network. The image data can also be provided to one or more neural networks to generate embeddings for the images. The neural networks that process the images can include a convolution neural network. Each of the embeddings for the textual data and the image data can provide descriptors for one or more portions of each document and/or image that is provided to the multimodal deep learning model. The resulting embeddings can be provided as inputs to a trained model, also referred to as an attention model, for determining the embeddings that should be given more consideration than others. For instance, the embeddings, or connections between embeddings, can be assigned weights by the attention model according to their relevance to a particular diagnosis or a clinical decision.

The multimodal deep learning model can include multiple subsystems for providing diagnoses. For instance, the multimodal deep learning model can include an input processing module, a memory component, an attention model, and an output generation module, which can provide a final representation of a diagnosis in a form that is preferred by a clinician (i.e., a user). The input processing module can analyze different types of inputs, and the analysis performed by the input processing module can be selected according to the type of input. For instance, the input processing module can perform separate analyses for text inputs, image inputs, multi-class and multi-label inputs, multi-class and single label inputs, single diagnosis inputs, section-engineered inputs, and/or section specific inputs with limited descriptors. In this way, embeddings for the inputs can be tailored to promote efficiency and accuracy.

The memory component of the multimodal deep learning model can be provided with a predefined structure for more effectively identifying values when responding to a query. For instance, the memory component can be a condensed memory network with an abstract level of learned memory. Associations between memory slots and/or memory values can be predefined by a clinician or other expert, or learned from available data (e.g., any data available to the multimodal deep learning model). Furthermore, the memory component can be updated based on frequency data pertaining to each diagnosis available from the multimodal deep learning model. The frequency data can be based on public sources (e.g., a medical websites) and/or private sources (clinical electronic health records (EHRs)). Memory values that are less frequently accessed can be ignored or re-written in order to preserve computational resources for those memory values that remain relevant over time.

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the representative embodiments. Such methods and apparatus are clearly within the scope of the claimed invention.

Figure 1:
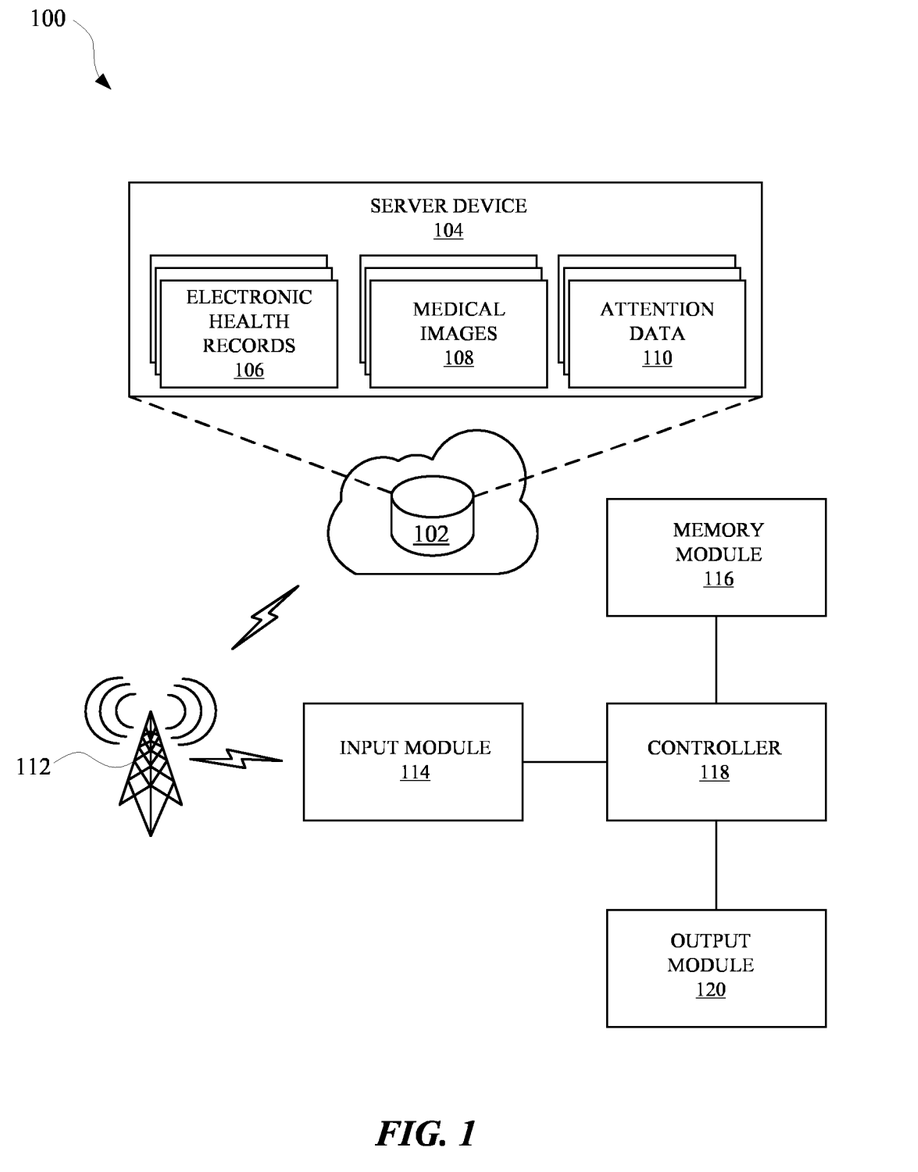
FIG. 1 illustrates a system for providing medical diagnoses using a multimodal deep learning model.

FIG. 1 illustrates a system 100 for providing medical diagnoses using a multimodal deep learning model. The system 100 can be embodied as one or more computing devices that execute instructions available to the computing devices. The system 100 can include one or more remote devices 102, such as a server device 104 and/or any other storage device, for providing medical-related data for assisting with identifying accurate medical diagnoses. The server device 104 can provide an input module 114 with access to electronic health records 106, medical images 108, and/or attention data 110. The electronic health records 106 can include medical data corresponding to current and prior patient diagnoses, as well as general sources of medical information. Such sources can include medical-related websites and databases that can include text and images for assisting clinicians with determining patient diagnoses. Furthermore, the medical images 108 (e.g., X-rays, CT scans, MRI, etc.) can be included in the electronic medical records 106 and/or separate from the electronic medical records 106. For instance, the medical images 108 can be associated with a particular patient and include labels that identify a diagnoses of the patient. Furthermore, the medical images 108 can include no labels, but otherwise be associated with a patient that has a particular diagnosis, which can be determined from a source of the medical images 108 (e.g., an electronic folder or other source that is associated with the patient).

The attention data 110 provided by the server device 104 can correspond to data that is indicative of an amount of time clinicians spend looking at the electronic health records 106 and/or the medical images 108 when preparing a diagnosis for a patient. For instance, a computing device operated by the clinician can include a camera that can track the eye movement of the clinician. The computing device can also record the arrangement of the electronic health records 106 and/or the medical images 108 at a display of the computing device. The computing device and/or the server device 104 can use sensor data (e.g., based on signals provided by a camera) related to clinician eye movement, data related to the arrangement of the records and images at the display, data related to screen taps or mouse movement, and/or any other attention-related data to generate correlations that can be used as the basis for the attention data 110. For instance, when a patient experiences a broken rib, the clinician may spend more time examining an x-ray image than a textual document, therefore the attention data 110 can indicate that the clinician relied more on the image than the textual document when making the broken rib diagnosis.

In some implementations, multiple electronic health records 106 can be associated with a particular diagnosis, and the attention data 110 can indicate the electronic health records 106 that clinicians accessed the most when making the particular diagnoses. For example, a patient with a diagnoses of lung cancer can be identified in an electronic medical record 106 as having complained of chest pain, hemoptysis, and difficulty swallowing. The attention data 110 can indicate that the clinician who provided the diagnosis viewed an article on lung cancer more than an x-ray image of the patient's lungs or an article on pneumonia. In some implementations, the attention data 110 can identify portions of an individual electronic health record 106 that the clinician viewed the most when preparing a diagnosis. For instance, the attention data 110 can identify a first section of an article as being given more attention by a clinician than a second section of the article, at least when preparing a particular diagnosis. In this way, the system 100 is able to determine, using the attention data 110, the portions of the electronic health records 106 and/or the medical images 108 that were most relevant for making a particular diagnosis (e.g., a section of a document entitled "conditions" can be more relevant to a diagnosis for a clinician than a "causes" section).

The electronic health records 106, the medical images 108, and/or the attention data 110 can be provided to an input module 114 of the system 100. The remote device 102 can communicate such data over a network 112, which can be a private or public network, such as the internet. The input module 114 can use the electronic health records 106, the medical images 108, and/or the attention data 110 to generate embeddings for each of the different inputs. The embeddings can correspond to vectors that link different portions of the inputs. The embeddings can be generated using one or more neural networks such as a recurrent neural network, a bi-directional recurrent neural network, a convolutional neural network, and/or any other neural network capable of providing embeddings for an input. In some implementations, a convolutional neural network can learn from existing text descriptors associated with the medical images 108 in order to generate embeddings from the images for subsequent use by the system 100.

The embeddings generated by the input module can be used by a controller 118 to update a memory module 116. The memory module 116 can include a predefined structure to optimize the selection of memory keys and values. For instance, the memory keys and values can be organized according to a frequency that particular information in memory is accessed or otherwise modified. Information that is less frequently accessed can be replaced or otherwise omitted from the memory module 116 in order to preserve computational resources and increase an amount of available space at the memory module 116.

Memory slots of the memory module 116 can each correspond to a key-value embedding that is generated at the input module 114. For instance, when image data is provided to the input module 114, embeddings for the image data can be generated for one or more portions of the image data. Furthermore, word embeddings for the image data can also be generated and stored as value embeddings that are correlated to key embeddings. Similarly, when textual data inputs are provided to the input module 114, embeddings can be generated for the textual data. The key embeddings can be correlated to content of the textual data and the value embeddings can be correlated to titles, section headings, and/or any other identifier that can indicate a section of text in the textual data.

The controller 118 can be tasked with reading and writing to the memory module 116, in order to update that memory module 116 and provide responses to queries provided to the input module 114. Furthermore, the controller 118 can assign frequency data to the key embeddings and/or value embeddings for particular diagnosis in order to direct the attention to the most relevant memory slots when responding to a query. When a frequency corresponding to a memory slot reaches or exceeds a threshold value (e.g., a low frequency threshold value), the memory slot can be deleted and/or reused in order to save space and improve the speed of the system 100.

Figure 2:
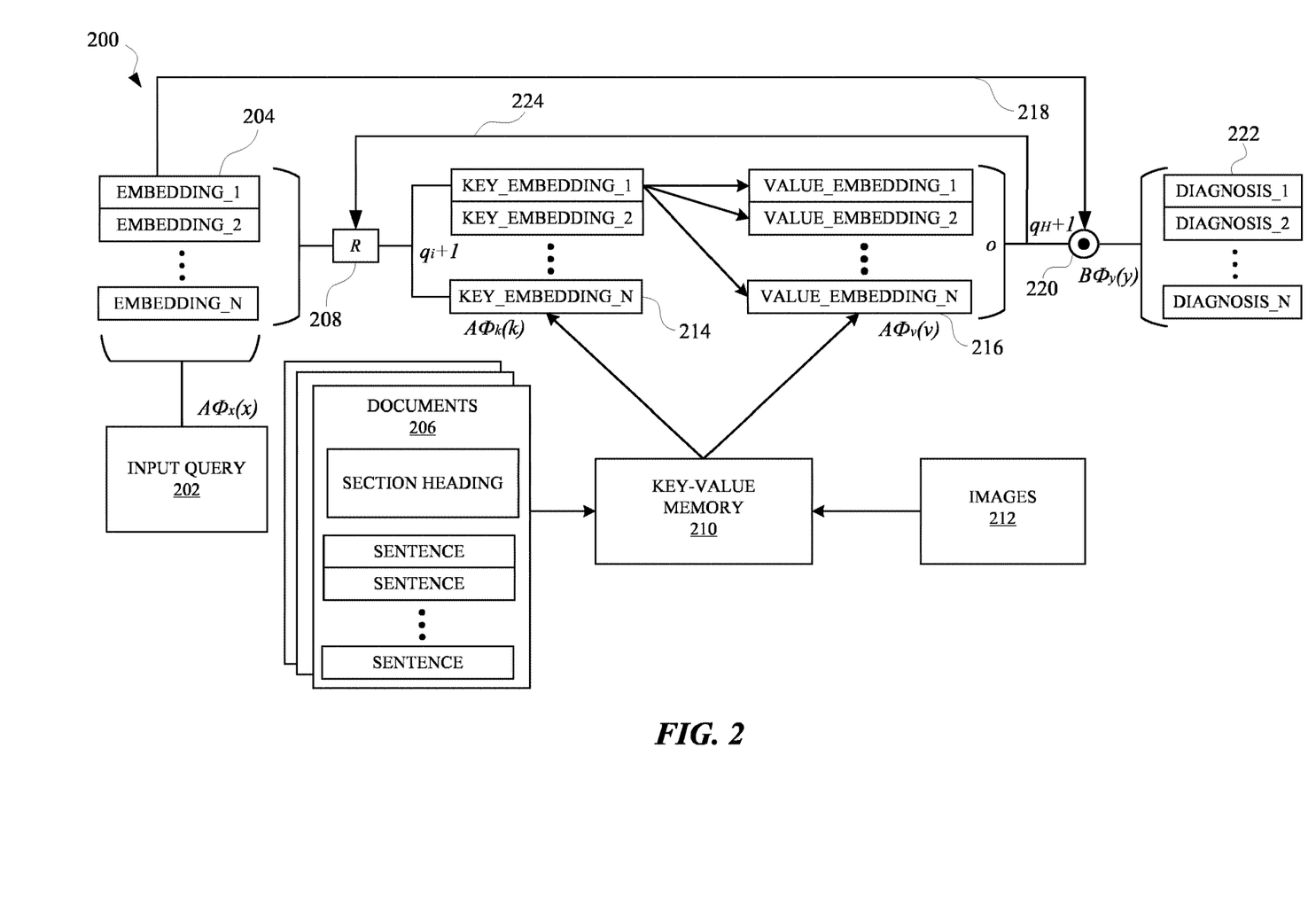
FIG. 2 illustrates an implementation of a multimodal deep memory network as discussed herein.

FIG. 2 illustrates an implementation of a multimodal deep memory network 200 as discussed herein. The multimodal deep memory network 200 can include a key-value memory 210 that stores key embeddings 214 and value embeddings 216. The key embeddings 214 and value embeddings 216 can correspond to embeddings generated from different input mediums such as documents 206 and/or images 212. The documents 206 can be processed according to their various parts (e.g., section headings and sentences) by a neural network, such as a bi-directional neural network process, a convolutional neural network process, a bag of words neural network process, and/or any other process capable of encoding text. Similarly, the images 212 can be processed through a convolutional neural network process in which key embeddings 214 and value embeddings 216 are generated from the images 212.

Addressing the key value memory 210 can include measuring a probability that a document 206 or image 212, or a portion thereof, is similar to each existing key according to Equation (1) below, where $A\Phi_x(x)$ is the input n (e.g., a document 206 or image 212, or portion thereof). Each probability can then be attached to a memory slot accordingly.

$$ph_i = \text{Softmax}(A\Phi_x(x) \cdot A\Phi_K(kh_i)) \tag{1}$$

In Equation (1), $\Phi$ can correspond to feature maps of dimension D, and Equation (2) can provide the equation for Softmax.

$$\text{Softmax} = e^{z_i}/\Sigma_j e^{z_j} \tag{2}$$

Using the probabilities calculated according to Equation (1), an output vector corresponding to a weighted sum of the memory slot values can be calculated from Equation (3) below.

$$o = \Sigma_i ph_i A\Phi(vh_i) \tag{3}$$

After calculating the output vector, the embedding(s) associated with the document 206 or image 212 can be updated with Equation (4) below, where R is adxd matrix.

$$n_{i+1} = R_i(n_i + o) \tag{4}$$

The steps corresponding to Equations (1), (3), and (4) can be repeated for a fixed number of hops 224. A probability for each available patient diagnosis is computed using the resulting output vector over all possible diagnoses $\gamma_i$, according to Equation (5) below, where B can be a d×D matrix. The multimodal deep memory network 200 can be trained this way, through an end to end process. In some implementations, back propagation and/or stochastic gradient descent are used to learn the parameters A, B and $R_1, \ldots, R_H$.

$$p = \text{sigmoid}(n_{H+1}^T B \Phi_\gamma \gamma_i) \quad (5)$$

If an input, such as a document 206 and/or image 212 is related to multiple memory slots, the number of hops 224 to identify all the related memory slots can be numerous, and potentially result in some related memory slots not being identified. For instance, an input can be associated with multiple different diagnoses, and some of the diagnoses can be correlated together by the multimodal deep memory network 200. Therefore, a different approach to addressing the key value memory 210 can include incorporating multi-layer feedforward neural network (FNNs), which can employ a sigmoid output layer instead of Softmax. Each FNN can calculate a weight between 0 and 1 for each memory slot of the key value memory 210, in order that the multimodal deep memory network 200 can thereafter read the weighted sum of the memory values.

Documents 206 provided to the multimodal deep memory network 200 can be represented in a Bag of Words (BOW) representation, in which each word $w_{ij}$ in the document 206 (i.e., $d_i = w_{i1}, w_{i2}, w_{i3}, \ldots w_{in}$) is represented as embeddings. The embeddings can be summed to create a result vector provided in Equation (6) below, where A is the embedding matrix.

$$\Phi(d_i) = \Sigma_j A w_{ij} \quad (6)$$

Alternatively, the documents 206 can be encoded according to a position encoding process in which the position of the words in the documents 206 are encoded. The encoding can be implemented through Equation (7) below, in which • is an element-wise multiplication. Furthermore, $l_j$ is a column vector with a structure $$l_{kj} = \left(1 - \frac{j}{J}\right) - \left(\frac{k}{d}\right)\left(\frac{2j}{J}\right),$$

with J being the number of words in a document 206 and d being the dimensions of the embeddings. It should be noted that the key embeddings 214 and the value embeddings 216 can also be represented in this way.

The multimodal deep memory network 200 can process a variety of different inputs, and continue training as new inputs are received. Training input types can include image-only data, text-only data, multi-document data where each document contains multiple diagnoses, multi-document data where each document contains a single diagnosis, binary classification data where a single diagnoses is indicated with a binary value (e.g., yes or no), section-engineered data having single important section or label, and/or a document with a single label (e.g., a section heading) and a limited number of words. In some implementations, what constitutes an important section or feature of an input (e.g., a document or image) can be based on attention metrics or attention data. The attention data can be based on an amount of consideration that was previously given to an input to the multimodal deep memory network 200 or a portion of input to the multimodal deep memory network 200. For instance, the attention data can be based on an amount of eye movement that was directed at a document or image while compiling a diagnosis for a patient.

In order to generate a patient diagnosis 222 from an input query 202, the input query 202 can be processed by the multimodal deep memory network 200 to generate embeddings 204 from the input query 202. A residual connection 218 to the embeddings 204 can be provided by the multimodal deep memory network 200 in order to mitigate abstraction of the input embeddings 204 as an increasing number of hops 224 are performed.

The multimodal deep memory network 200 can provide, as output, a patient diagnosis 222, which can be embodied as a single classification diagnosis or a sequence of words (e.g., DIAGNOSIS_1, DIAGNOSIS_2, DIAGNOSIS_N, etc.). For instance, the single classification can be identified as a most probable diagnosis according to the multimodal deep memory network 200. The sequence of words approach to providing a patient diagnosis 222 can be based on a recurrent neural network. The patient diagnosis 222 can be represented in one or more different mediums according to a preference of an end user (e.g., a clinician or patient), or a learned medium that is identified through training of the multimodal deep memory network 200. The different mediums can include documents, videos, images, sound, and/or any other medium through which an end user can understand a predicted patient diagnosis 222.

Figure 3:
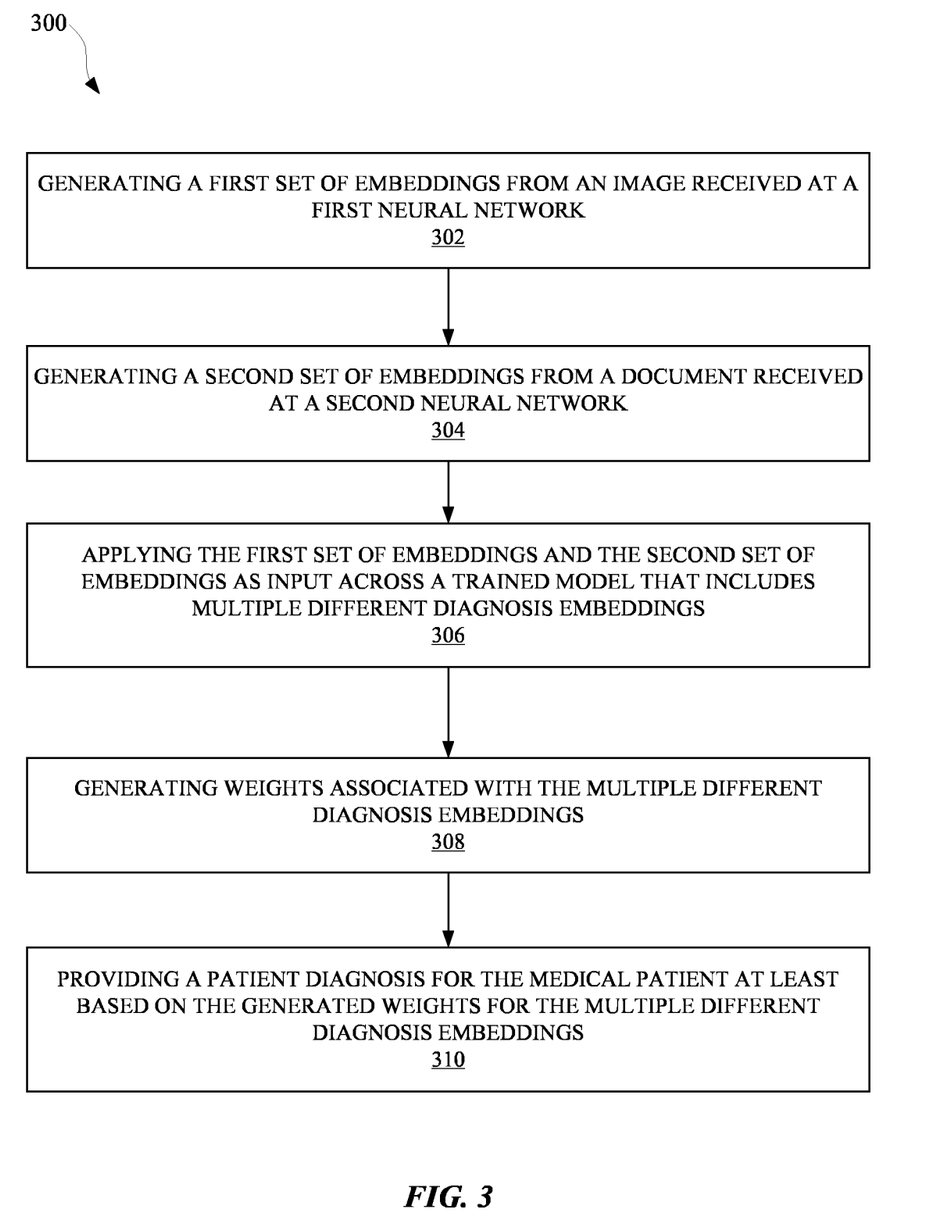
FIG. 3 illustrates a method for providing a patient diagnosis from a multimodal deep memory network according to a correlation between embeddings provided at the multimodal deep memory network.

FIG. 3 illustrates a method 300 for providing a patient diagnosis from a multimodal deep memory network according to a correlation between embeddings provided by the multimodal deep memory network. The method 300 can be performed by one or more computing devices, network devices, and/or any other device capable of performing functions of one or more different neural networks. The method 300 can include a block 302 of generating a first set of embeddings from an image received at a first neural network. The first set of embeddings can be generated using a neural network, such as a convolution neural network having one or more hidden layers. The first set of embeddings can include key embeddings corresponding to image features, and value embeddings corresponding to labels or text associated with the image.

The method 300 can further include a block 304 of generating a second set of embeddings from a document received at a second neural network. The second neural network can be a recurrent neural network or a bi-directional recurrent neural network that updates vector and/or matrices weights according to forward passes and backward passes of neurons. The second set of embeddings can include value embeddings corresponding to section heading (e.g., a title) of the document and key embeddings corresponding to content that is separate from the section heading (e.g., sentences below the title).

The method 300 can further include a block 306 of applying the first set of embeddings and the second set of embeddings as input across a trained model that includes multiple different diagnosis embeddings. The trained model can include key embeddings and value embeddings that are weighted at least partially based on an amount of attention given to a portion of medical data from which the key embeddings and the value embeddings are generated. The trained model can include or access a condensed memory network that includes at least some amount of abstracted information. The trained model can include a predefined structure that is updated as memory slots in a memory of the trained model become less frequently accessed. In this way, less frequently accessed data can become more abstracted over time as the trained model undergoes subsequent training, and more frequently accessed data can remain less abstracted in order that more details can be gleaned from the more frequently accessed data.

The method 300 at block 308 can include generating weights associated with the multiple different diagnosis embeddings. Weights for the different diagnosis embeddings can be generated according to correlations between the embeddings generated from the image and/or document, and the diagnosis embeddings provided by the trained model. The resulting weights can be classified as a predetermined patient diagnosis or converted into a sentence over multiple iterations.

The method 300 can further include a block 310 of providing the patient diagnosis for the medical patient at least based on the generated weights for the multiple different diagnosis embeddings. The patient diagnosis can be provided in one or more mediums such as a document, image, video, sound, and/or any other medium through which a diagnosis can be communicated. For instance, the patient diagnosis can be embodied in a sentence or classification that is printed onto a document that includes additional detailed information about the patient diagnosis. The additional details can be provided from the trained model, at least based on correlations between the patient diagnosis and the key embeddings and/or value embeddings accessible to the trained model.

Figure 4:
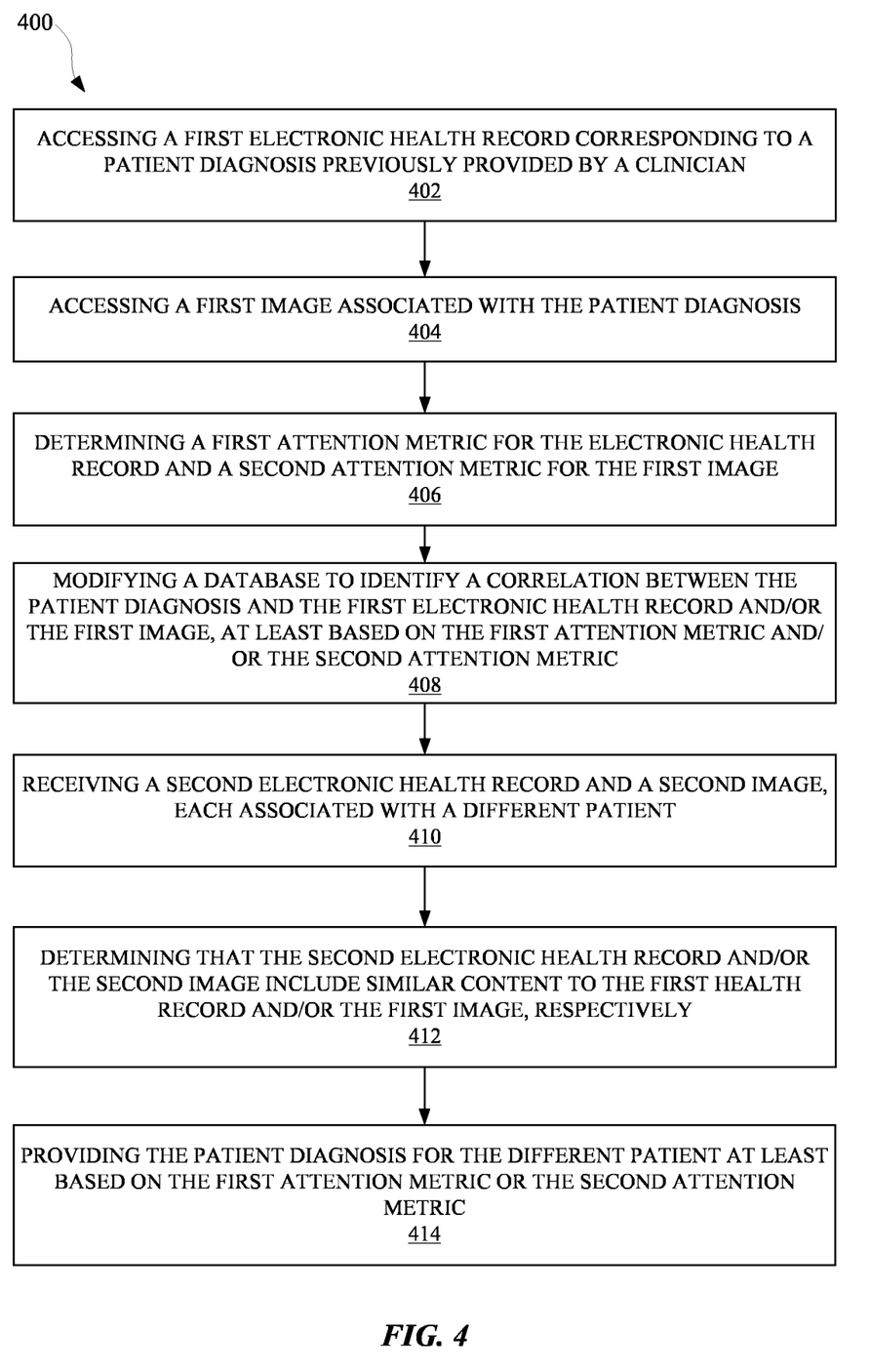
FIG. 4 illustrates a method for providing a patient diagnosis using a multimodal deep memory network that provides weights for certain data according to an amount of attention previously given to the data when creating a previous patient diagnosis.

FIG. 4 illustrates a method 400 for providing a patient diagnosis using a multimodal deep memory network that provides weights for certain data according to an amount of attention previously given to the data when creating a previous patient diagnosis. The method 400 can be performed by one or more computing devices, network devices, and/or any other device capable of performing functions of a neural network. The method 400 can include a block 402 of accessing a first electronic health record corresponding to a patient diagnosis previously provided by a clinician. The first electronic health record can be an electronic document that includes headings and text (e.g., sentences) that identify the patient diagnosis, as well as information related to the patient diagnosis such as, for example, symptoms and test results. The first electronic health record can be stored in a database on a computing device that is separate from, or the same as, the computing device that operates the multimodal deep memory network. Furthermore, the first electronic health record can be authored by the clinician or generated through an automated process that compiles the first electronic health record from a variety of sources. For instance, an electronic health record can be generated through an automated process that uses historical patient data from a variety of sources in order to generate a single file of health data for a patient.

The method 400 can further include a block 404 of accessing a first image associated with the patient diagnosis. Each of the first electronic health record and the first image can correspond to a patient, or multiple patients, that received the patient diagnosis. For instance, the patient diagnosis can be Alzheimer's disease and the first image can be data from a magnetic resonance imaging (MRI) scan of the patient. In some implementations, the first image can include labels or other text that identify portions of the first image. Alternatively, the first image can be associated with metadata that can provide descriptions about different portions of the image, and/or identify the clinician, patient, and/or any other data relevant to the patient diagnosis. The first image can be provided from the same source as the first electronic health record, or a different source (e.g., the computing device that controls the MRI scanning).

The method 400 can also include a block 406 of determining a first attention metric for the first electronic health record and a second attention metric for the first image. The first attention metric and the second attention metric can be data that quantifies an amount of attention or consideration given to the first electronic health record and the second attention metric respectively. For instance, the first attention metric and the second attention metric can be based on sensor data provided by a camera of a computing device. An application at the computing device can receive signals from the camera and use the signals to identify eye movements of a user of the computing device. The application can determine an amount of time spent looking at particular documents and/or images, such as the first electronic health record and the first image.

The first attention metric and the second attention metric can be based on the eye movements of a user that was observing each of the first electronic health record and the first image, respectively. In some implementations, the computing device can track amounts of time that the first electronic health record and the first image were opened at the computing device or a separate computing device. These times can be used as a basis for generating the first attention metric and the second attention metric. In this way, the multimodal deep memory network can assign weights to key embeddings and/or value embeddings according to the consideration given to them. For instance, the first attention metric and the second attention metric can indicate that a clinician spent more time viewing the first image before generating a diagnosis than looking at the first electronic health record (e.g., a medical history document). As a result, a weight of a key embedding and/or value embedding corresponding to the first image can reflect the consideration given to the first image compared to the electronic health record.

The method 400 at block 408 can include modifying a database to identify a correlation between the patient diagnosis and the first electronic health record and/or the first image, at least based on the first attention metric and/or the second attention metric. The database can be part of a memory module incorporated into the multimodal deep memory network. The database can include key embeddings and value embeddings corresponding to one or more electronic health records and/or images from one or more sources. Furthermore, the database can include medical reference data provided from multiple different sources such as, for example, websites, electronic documents, and/or any other sources for medical data.

The method 400 at block 410 can include receiving a second electronic health record and a second image, each associated with a patient that is different from the patient associated with the first electronic health record and the first image. The second electronic health record and the second image can be processed by an input module of the multimodal deep memory network in order to generate key embeddings and/or value embeddings. The method 400 at block 412 can include determining that the second electronic health record and/or the second image include similar content to the first electronic health record and/or the first image, respectively. Block 412 can be performed by comparing key embeddings and/or value embeddings. Furthermore, block 412 can be performed by processing weighted connections between key embeddings and/or value embeddings.

The method 400 can further include a block 414 of providing, by the multimodal deep memory network, the patient diagnosis for the different patient at least based on the first attention metric or the second attention metric. For instance, the first image can be correlated to key embeddings and/or value embeddings that identify the patient diagnosis, and the second attention metric can indicate that the clinician spent more time observing the first image than the first electronic health record when making the patient diagnosis. Therefore, the patient diagnosis provided to the different patient can be based on an amount of consideration given by experts to particular medical data. Furthermore, the multimodal deep memory network leverages the attention metrics in order to improve confidence between queries input to the multimodal deep memory network and patient diagnoses output by the multimodal deep memory network.

Figure 5:
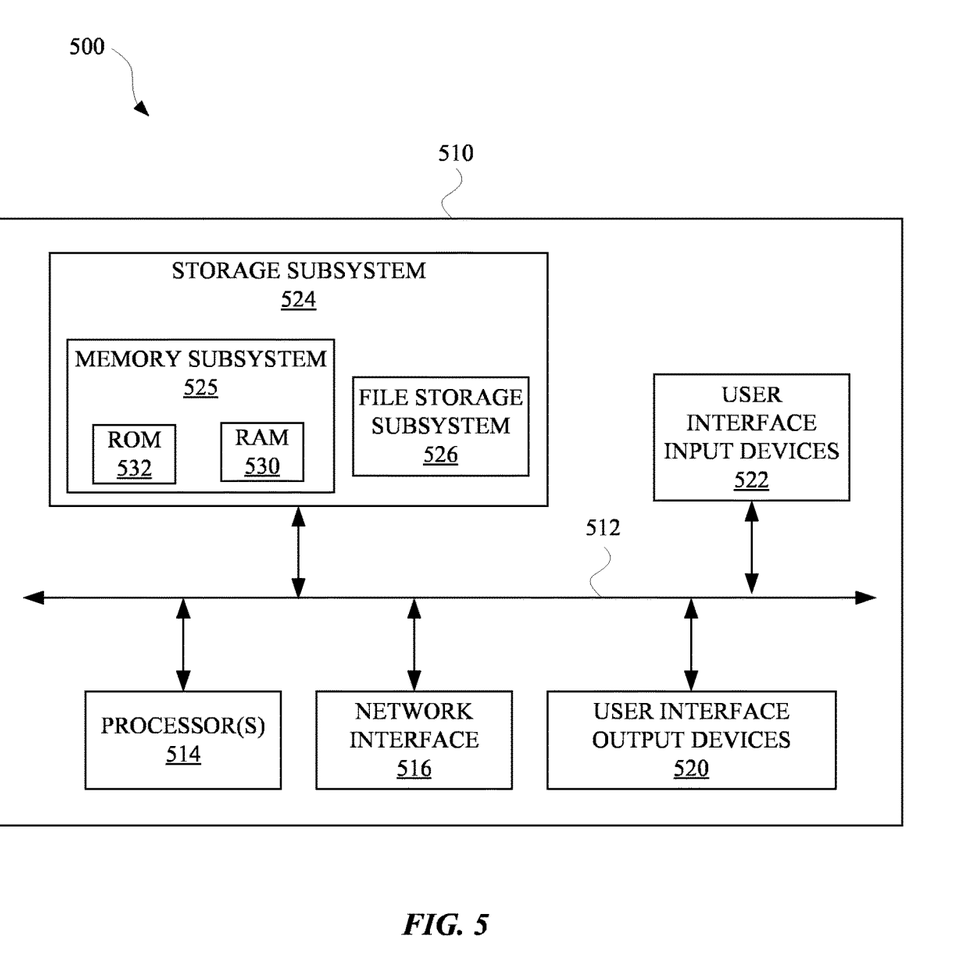
FIG. 5 is a block diagram of an example computer system.

FIG. 5 is a block diagram of an example computer system 510. Computer system 510 typically includes at least one processor 514 which communicates with a number of peripheral devices via bus subsystem 512. These peripheral devices may include a storage subsystem 524, including, for example, a memory 525 and a file storage subsystem 526, user interface output devices 520, user interface input devices 522, and a network interface subsystem 516. The input and output devices allow user interaction with computer system 510. Network interface subsystem 516 provides an interface to outside networks and is coupled to corresponding interface devices in other computer systems.

User interface input devices 522 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 510 or onto a communication network.

User interface output devices 520 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 510 to the user or to another machine or computer system.

Storage subsystem 524 stores programming and data constructs that provide the functionality of some or all of the modules described herein. For example, the storage subsystem 524 may include the logic to perform selected aspects of method 300, method 400, the multimodal deep memory network 200, and/or to implement one or more of the remote device 102, server device 104, controller 118, and/or any other implementation discussed herein.

These software modules are generally executed by processor 514 alone or in combination with other processors. Memory 525 used in the storage subsystem 524 can include a number of memories including a main random access memory (RAM) 530 for storage of instructions and data during program execution and a read only memory (ROM) 532 in which fixed instructions are stored. A file storage subsystem 526 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 526 in the storage subsystem 524, or in other machines accessible by the processor(s) 514.

Bus subsystem 512 provides a mechanism for letting the various components and subsystems of computer system 510 communicate with each other as intended. Although bus subsystem 512 is shown schematically as a single bus, alternative implementations of the bus subsystem may use multiple busses.

Computer system 510 can be of varying types including a workstation, server, computing cluster, blade server, server farm, or any other data processing system or computing device. Due to the ever-changing nature of computers and networks, the description of computer system 510 depicted in FIG. 5 is intended only as a specific example for purposes of illustrating some implementations. Many other configurations of computer system 510 are possible having more or fewer components than the computer system depicted in FIG. 5.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A method of querying a trained memory network performed by one or more processors, the method comprising:

generating a first set of embeddings from an image received at a first neural network;

generating a second set of embeddings from a document received at a second neural network, wherein each of the image and the document are associated with a medical patient;

applying the first set of embeddings and the second set of embeddings as input across the trained memory network, the memory network including a key-value memory and including multiple different diagnosis embeddings, the key-value memory including memory-slots each according to a key embedding and a value embedding;

generating weights for the multiple different diagnosis embeddings based on a correlation between the first set of embeddings and the second set of embeddings, and the key embeddings and the value embeddings; and providing a patient diagnosis for the medical patient at least based on the generated weights for the multiple different diagnosis embeddings.

2. The method of claim 1, wherein applying the first set of embeddings and the second set of embeddings as input across the trained memory network comprises iteratively updating an input embedding based on key embeddings and value embeddings of memory-slots of the key-value memory to obtain the correlation between the first set of embeddings and the second set of embeddings, and the key embeddings and the value embeddings.

3. The method of claim 2, wherein updating the input embedding based on key embeddings and value embeddings of memory-slots of the key-value memory comprises determining a weight of a value embedding of a memory-slot, said weight measuring a similarity of a key embedding of the memory-slot to the input embedding, and computing an updated input embedding based on the weight and the value embedding.

4. The method of claim 3, wherein determining the weight of a value embedding of a memory-slot comprises calculating the weight using a multi-layer feedforward neural network.

5. The method of claim 2, wherein generating a weight for a diagnosis embedding comprises applying a sigmoid function to the iteratively updated input embedding and the diagnosis embedding.

6. The method of claim 1, wherein the memory network includes weights that are based at least in part on an amount of attention given to a portion of medical data from which the key embeddings and the value embeddings were generated.

7. The method of claim 1, wherein the amount of attention given to a portion of medical data comprises data indicating an electronic health record that a clinician accessed when making a diagnosis.

8. The method of claim 1, wherein the amount of attention corresponds to attention data that is based on an amount of eye movement exhibited by a user accessing the medical data.

9. The method of claim 1, wherein generating the second set of embeddings includes generating an input value embedding from a section heading of the document, and generating input key embeddings from content that is separate from the section heading of the document.

10. The method of claim 1, wherein key embeddings and data embeddings of the key-value memory are generated at least in part based on medical data from a medical-related website or a database for assisting clinicians with determining patient diagnoses.

11. The method of claim 1, wherein key embeddings and data embeddings of the key-value network are generated at least in part from a medical image with a corresponding textual description.

12. The method of claim 1, wherein the second neural network is a bi-directional recurrent neural network, and the document corresponds to an electronic health record.

13. The method of claim 1, wherein the first neural network is a convolutional neural network.

14. A computing device for querying a trained memory network, comprising:
one or more processors; and
memory configured to store instructions that, when executed by the one or more processors cause the one or more processors to perform steps that include:
generating a first set of embeddings from an image received at a first neural network;
generating a second set of embeddings from a document received at a second neural network, wherein each of the image and the document are associated with a medical patient;
applying the first set of embeddings and the second set of embeddings as input across the trained memory network, the memory network including a key-value memory and including multiple different diagnosis embeddings, the key-value memory including memory-slots each according to a key embedding and a value embedding;
generating weights for the multiple different diagnosis embeddings based on a correlation between the first set of embeddings and the second set of embeddings, and the key embeddings and the value embeddings; and
providing a patient diagnosis for the medical patient at least based on the generated weights for the multiple different diagnosis embeddings.

15. A non-transitory computer-readable medium configured to store instructions for querying a trained memory network that, when executed by one or more processors, cause the one or more processors to perform steps that include:
generating a first set of embeddings from an image received at a first neural network;
generating a second set of embeddings from a document received at a second neural network, wherein each of the image and the document are associated with a medical patient;
applying the first set of embeddings and the second set of embeddings as input across the trained memory network, the memory network including a key-value memory and including multiple different diagnosis embeddings, the key-value memory including memory-slots each according to a key embedding and a value embedding;
generating weights for the multiple different diagnosis embeddings based on a correlation between the first set of embeddings and the second set of embeddings, and the key embeddings and the value embeddings; and
providing a patient diagnosis for the medical patient at least based on the generated weights for the multiple different diagnosis embeddings.

16. The non-transitory computer-readable medium of claim 1, wherein the amount of attention is based attention data that is based on an amount of eye movement exhibited by a user accessing the medical data.

17. The non-transitory computer-readable medium of claim 1, wherein generating the second set of embeddings includes generating an input value embedding from a section heading of the document, and generating input key embeddings from content that is separate from the section heading of the document.

18. The non-transitory computer-readable medium of claim 1, wherein the medical data, from which the key embeddings and the value embeddings are generated, includes a medical image with a corresponding textual description.

19. The method of claim 1, further including: measuring a probability that a document, an image, a portion of the document, or a portion of the image is similar to each existing key.

20. The method of claim 19, further including: attaching each of the probabilities to a corresponding one of the memory slots.

* * * * *